(12) United States Patent
Warren, Jr.

(10) Patent No.: US 6,348,042 B1
(45) Date of Patent: Feb. 19, 2002

(54) BIOACTIVE SHUNT

(76) Inventor: W. Lee Warren, Jr., 804 Wible Run Rd., Pittsburgh, PA (US) 15209

( * ) Notice: Subject to any disclaimer, the term of this patent is extended or adjusted under 35 U.S.C. 154(b) by 0 days.

(21) Appl. No.: 09/241,690

(22) Filed: Feb. 2, 1999

(51) Int. Cl.⁷ .................. A61M 5/00; A61M 25/00; A61L 3/00; B05D 3/00; A61K 38/43
(52) U.S. Cl. .................. 604/8; 604/6.16; 604/266; 427/2.25; 424/94.1; 424/94.2; 424/94.3; 424/94.6; 424/570
(58) Field of Search .................. 604/8–10, 264–266, 604/523, 6.16; 424/422–426, 484, 486, 400, 405, 487–491, 520, 529, 537, 570, 94.1–94.3, 94.6, 94.63–94.64; 427/2.1, 2.24, 2.25, 2.28; 523/111–112, 105, 122, 200; 623/1.44–1.48, 11, 12

(56) References Cited

U.S. PATENT DOCUMENTS

| | | | | |
|---|---|---|---|---|
| 4,378,435 A | * | 3/1983 | Takagi et al. | ................ 435/180 |
| 5,059,654 A | * | 10/1991 | Hou et al. | |
| 5,338,770 A | * | 8/1994 | Winters et al. | ............. 523/112 |
| 5,531,735 A | * | 7/1996 | Thompson | ................ 604/891.1 |
| 5,594,136 A | * | 1/1997 | Sessler et al. | |
| 5,616,338 A | * | 4/1997 | Fox, Jr. et al. | ............. 424/423 |
| 6,136,024 A | * | 10/2000 | Shimizu | |
| 6,166,173 A | * | 12/2000 | Mao et al. | |
| 6,184,266 B1 | * | 2/2001 | Ronan et al. | |

* cited by examiner

Primary Examiner—Angela D. Sykes
Assistant Examiner—Patricia Bianco
(74) Attorney, Agent, or Firm—Debra M. Parrish

(57) ABSTRACT

The present invention relates to a shunt, and a method for treating catheters, more particularly shunts, wherein the catheter is made of a biocompatible material and adapted at least for insertion into the brain of a living organism and enzymes are impregnated, either directly or through a matrix forming system, into the interior of the lumen of the catheter. The enzymes impregnated have at least one of the following characteristics: (1) they require a confirmational form and either completely or substantially lose their activity upon dislocation from the interior of the lumen; (2) they require the presence of co-factors for activation which co-factors are also present in the interior of the lumen but are not otherwise present in the biological system in sufficient quantity to excite activation of the impregnated enzymes.

20 Claims, No Drawings

BIOACTIVE SHUNT

BACKGROUND OF THE INVENTION

The use of biocompatible long-term implanted shunts has become more prevalent as a treatment modality for a variety of illnesses and diseases.

For example, the development of shunts for the treatment of hydrocephalus was a major advance in neurosurgery. Shunting has such a dramatic effect on the natural history of hydrocephalus that it is the sole treatment used for many causes of hydrocephalus. The placement of a cerebrospinal fluid shunt is now the third most commonly performed neurosurgical procedure in the United States annually and the most common pediatric neurosurgical procedure. Nonetheless, shunts are plagued with the highest complication rate of all neurosurgical procedures.

The one and five year failure rates for CSF shunts have been reported to be between 20–30% and 23–49%, respectively. The most common reason for shunt failure is obstruction of the catheter. Proximal obstruction accounts for nearly half of all failures in most reported series while distal obstruction accounts for up to 35% of obstructions. Blockage of the valve also is a common problem. Some catheters are blocked at multiple sites.

The specific cause of failure for a given catheter appears to be a function of time. The vast majority of infections, valve-problems, or proximal obstructions requiring catheter removal occur within two years of insertion. Catheters that fail after two years are obstructed distally more than two-thirds of the time.

The materials responsible for obstruction are varied. Typically, the proximal catheter is blocked by ingrowth of choroid plexus or glial tissue, or obstructed by blood or cellular debris. Distally, the peritoneum can grow into the catheter and obstruct its lumen.

Neurosurgeons often encounter the problem of shunt failure. In the pediatric myelomeningocele population, one frequently encounters patients who have undergone dozens of shunt revisions. The combined neuropsychological, economic, and psychosocial impact of multiple shunt failures and revisions on the life of a given patient is profound.

A number of inventions have been directed towards preventing the obstruction of hydrocephalus shunts. See e.g., Stati et al., U.S. Pat. No. 3,829,903; Labianca, U.S. Pat. No. 4,375,816; Ahmed, U.S. Pat. No. 5,728,061; Wong et al., U.S. Pat. No. 5,000,731; Schulte et al., U.S. Pat. No. 4,636,194; Corbett, U.S. Pat. No. 4,655,745; Hooven et al., U.S. Pat. No. 4,601,724; Schulte et al., U.S. Pat. No. 4,560,375; Wortman et al., U.S. Pat. No. 3,690,323; and Ames, U.S. Pat. No. 3,452,757. Each of those inventions uses a mechanical means to prevent blockage.

Other inventions use enzymes to prevent obstruction of a catheter lumen. For example, Van Anterwerp, U.S. Pat. No. 5,505,713, describes a process for producing a catheter and a catheter with a stable enzyme coating to prevent and dissolve fibrin or lipid-based obstructions within the lumen of the catheter. The means for attaching the enzymes is a polymer, an encapsulation method or a cross-linked matrix. The attachment means controls the rate of enzyme degradation. However, Van Anterwerp provides for the coating of the external surface of the catheter that is indwelling in the patient, not the lumen interior surface. Accordingly, the catheter and process described in Van Anterwerp is contraindicated for a shunt to be placed in cranial cavity where enzymatic degradation of externally contacting brain matter would be unacceptable.

Various patents to Guire, U.S. Pat. Nos. 3,959,078, 5,263,992 and 5,217,492 describe a system for attaching and stabilizing enzymes in a matrix. However, they do not use a hydrogel or other polymer matrix to bind the enzymes to the catheter and are limited in other important respects, e.g., specifies the use of specific biofunctional agent.

Similarly, Mosher, U.S. Pat. 5,114,413 describes the use of a proteinaceous material to coat the interior of a catheter, but is limited preventing blood components and cellular matter from adhering to the surface and is not directed to precluding the obstruction of the catheter lumen.

Thus, despite numerous and concerted efforts, a cost-efficient method has not been devised to create a biocompatible catheter that precludes shunt obstruction. In particular, despite the long felt need for such method or device in the cerebrospinal shunt industry, until Applicants' invention, no such method or device existed.

Accordingly, it is an object of this invention to provide a biocompatible catheter that degrades cellular material in the lumen of the catheter. It also is an object of this invention to provide a biocompatible catheter that degrades blood in the lumen of the catheter. It is also an object of the invention to provide a biocompatible catheter that degrades choroid plexus and peritoneum within its lumen. It is a further object of this invention to provide a catheter that degrades omentum within its lumen. It is an object of the present invention to provide a biocompatible catheter that is resistant to obstruction. It is a further object of this invention to provide a long-term placement biocompatible catheter that is resistant to obstruction. It is another object of this invention to provide for a CSF shunt that is resistant to obstruction. Other objects will be readily apparent based on the following detailed description taken with the figures.

DETAILED DESCRIPTION OF THE INVENTION

The present invention relates to a catheter in which the interior surface of the lumen is either impregnated with proteolytic enzymes or has an impregnated matrix layer of proteolytic enzymes that degrade biological material, including tissue, blood and cellular material, as it enters the catheter lumen. In a preferred embodiment, only the interior of the catheter lumen is impregnated with the proteolytic enzymes or has a matrix containing such enzymes. The enzymes, whether directly impregnated into the interior surface of the catheter lumen or an impregnated matrix thereto, are impregnated in such a manner that complete or partial detachment from the interior lumen of the catheter results in a loss. In a preferred embodiment of the invention, the attachment means for the enzymes is a matrix forming system which uses hydrogel or other polymers. The enzyme impregnation system may differ between proximal and distal catheters.

Further, because of the deleterious effect that free enzymes may have on tissue surrounding an implanted catheter, either at the proximal or distal end, an important characteristic of the enzymes used in the present invention is that upon separation and or dislocation from the interior surface of the catheter lumen, all substantial biological activity ceases.

Two characteristics of enzymes make them suitable for the present invention. First, enzymes must exist in a specific physical conformational state to retain their activity. Accordingly, enzymes can be chosen such that a portion of the enzyme that is required for impregnation directly into the catheter lumen surface or the matrix, is critical to the functionality of the enzyme such that if a non-impregnated portion of the enzyme is detached from the impregnated portion of the enzyme, the detached portion of the enzyme does not retain its conformational state and is inactive.

A second characteristic of enzymes that makes them suitable for the present invention is that enzymes require cofactors to catalyze most reactions. Preferably, the cofactor for the impregnated enzyme(s) is a substance normally not present, or present at concentrations below that which would be required to activate the enzyme impregnated in the lumen, within the biological system in which the catheter is inserted.

In one preferred embodiment, the catheter is also impregnated with a sufficient amount of an appropriate cofactor required by an impregnated enzyme. The catheter releases cofactor(s) at a rate to ensure an adequate concentration of cofactor in the lumen to incite enzymatic activity at appropriate intervals to preclude the growth of obstructing cellular material. Because of the required presence of the cofactor, if an impregnated enzyme, or a portion of an impregnated enzyme, is disengaged from the interior surface of the catheter lumen and exits the lumen, the absence of the cofactor, or the presence of the cofactor in too low a concentration, precludes the enzyme from catalyzing a reaction.

In one preferred embodiment, the interior surface of the catheter lumen is impregnated with urokinase or a matrix containing urokinase is impregnated onto the wall of the lumen to degrade blood. In another preferred embodiment, the interior surface of the catheter lumen is impregnated with proteases or a matrix containing proteases that is impregnated onto the wall of the lumen to degrade cellular material including cells of the choroid plexus or peritoneum. In yet another embodiment of the invention, the interior surface of the catheter lumen is impregnated with lipases or a matrix containing lipases that is impregnated onto the wall of the lumen. Other possible impregnants include collagenase and bacterial enzymes.

In yet another embodiment of the invention, the interior surface of the catheter lumen is impregnated with a combination of proteolytic enzymes which include lipases, proteases and urokinase, or a matrix containing such a combination.

In addition to the forgoing example of shunt application, the method of the current invention for modifying the inside of a catheter or tube has many potential applications in and outside of medicine. For example, any tube that must lie within a body cavity, e.g., vascular stents and medication pumps, has the potential to become obstructed but must be biocompatible with the tissue against which it lies. Non-medical devices that need to remain patent, e.g., sewer pipes and oil lines, could also utilize enzyme matrices to maintain their luminal patency.

What is claimed is:

1. A shunt, comprising:
    an elongated tubular element made of biocompatible material and adapted at least for insertion into the brain of a living organism;
    a surface coating applied solely to the interior lumen surface, said surface coating comprising a matrix-forming system; and
    at least one enzyme impregnated in said coating, wherein said enzyme requires a specific physical configuration for activation wherein said configuration is lost upon dislocation of said enzyme from said coating.
2. The shunt of claim 1, further comprising:
    an impregnated cofactor for said enzyme wherein said enzyme further requires said cofactor for activation.
3. The shunt of claim 1 or 2, wherein said matrix-forming system is a polymer.
4. The shunt of claim 1 or 2, wherein said matrix-forming system is a hydrogel.
5. A shunt, comprising:
    an elongated tubular element made of a biocompatible polymer and adapted at least for insertion into the brain of a living organism; and
    at least one enzyme impregnated solely in the interior lumen surface in said biocompatible polymer, wherein said enzyme requires a specific physical configuration for activation wherein said configuration is lost upon dislocation of said enzyme from said biocompatible polymer.
6. The shunt of claim 1, 5 or 2, wherein said enzyme is a proteolytic enzyme from the group of lipases, urokinase, trypsin, collengenase.
7. The shunt of claim 6 wherein said matrix-forming system is a polymer.
8. The shunt of claim 1, 5 or 2, wherein said enzyme is a bacterial enzyme.
9. The shunt of claim 8, wherein said matrix-forming system is a polymer.
10. A method for reducing the obstruction of a catheter lumen, comprising:
    coating solely the interior surface of said catheter lumen with a matrix-forming system;
    impregnating at least one enzyme in said matrix-forming system, wherein said enzyme requires a specific physical configuration for activation wherein said configuration is lost upon dislocation of said enzyme from said matrix-forming system.
11. A method of claim 10 further comprising:
    impregnating a cofactor for said enzyme wherein said enzyme requires said co-factor for activation.
12. A method of claim 10, wherein said enzyme is a proteolytic enzyme from the group of lipases, urokinase, trypsin, collengenase.
13. A method of claim 10, wherein said enzyme is a bacterial enzyme.
14. A method of claim 10, wherein said matrix-forming system is a polymer.
15. A method of claims 10, 11, 12 or 13, wherein said matrix-forming system is a hydrogel.
16. A shunt, comprising:
    an elongated tubular element made of a biocompatible polymer and adapted at least for insertion into the brain of a living organism;
    at least one enzyme impregnated solely in the interior lumen surface in said biocompatible polymer, wherein said enzyme requires a specific physical configuration for activation wherein said configuration is lost upon dislocation of said enzyme from said biocompatible polymer; and
    an impregnated cofactor for said enzyme wherein said enzyme further requires said cofactor for activation.
17. The shunt of claim 16 wherein said enzyme is a proteolytic enzyme from the group of lipases, urokinase, trypsin, collengenase.
18. The shunt of claim 16, wherein said enzyme is a bacterial enzyme.
19. The shunt of claims 16, 17 or 18 wherein said matrix-forming system is a polymer.
20. The shunt of claims 16, 17 or 18 wherein said matrix-forming system is a hydrogel.

* * * * *